United States Patent [19]

Gerardo

[11] Patent Number: 5,447,528

[45] Date of Patent: * Sep. 5, 1995

[54] METHOD OF TREATING SEASONAL AFFECTIVE DISORDER

[76] Inventor: Ernesto Gerardo, 9476 Greystone Pkwy., Brecksville, Ohio 44141

[ * ] Notice: The portion of the term of this patent subsequent to Mar. 8, 2011 has been disclaimed.

[21] Appl. No.: 207,650

[22] Filed: Mar. 7, 1994

Related U.S. Application Data

[62] Division of Ser. No. 427,984, Oct. 30, 1989, Pat. No. 5,292,345.

[51] Int. Cl.6 ................................................ A61N 5/00
[52] U.S. Cl. ...................................... 607/88; 607/91
[58] Field of Search .............................. 607/88–91; 600/26–27

[56] References Cited

U.S. PATENT DOCUMENTS

| 4,044,756 | 8/1977 | Hamilton | 607/90 |
| 4,858,609 | 8/1989 | Cole | 607/91 |
| 4,911,166 | 3/1990 | Leighton et al. | 607/90 |
| 5,292,345 | 3/1994 | Gerardo | 607/88 |

Primary Examiner—Angela D. Sykes
Attorney, Agent, or Firm—John R. Benefiel

[57] ABSTRACT

A method of treating Seasonal Affective Disorder is described using a portable photoneuronic energizer for providing a headworn portable full spectrum light source to treat Seasonal Affective Disorder comprising head support means, a full spectrum light mounted on a visor to be positioned to cause indirect light to enter the wearer's eyes.

1 Claim, 1 Drawing Sheet

METHOD OF TREATING SEASONAL AFFECTIVE DISORDER

CROSS REFERENCE TO RELATED APPLICATIONS

This is a divisional application of U.S. Ser. No. 07/427,984 filed on Oct. 30, 1989, now U.S. Pat. No. 5,292,345.

BACKGROUND OF THE INVENTION

Recent medical advances (*American Journal of Psychiatry*, Rosenthal et al, 142:2, 163-70) have demonstrated that light can be used to treat certain types of depression, specifically, Seasonal Affective Disorder (SAD). SAD is a condition in which an individual feels depressed and lethargic with a tendency to overeat, oversleep and crave carbohydrates. In its more severe forms, the affected person is totally withdrawn and unable to successfully function in society. This disorder is most commonly observed during the winter months, when skies are cloudy and overcast, with long periods of little or no natural sunlight exposure Many persons experiencing "winter blues", or "cabin fever" are probably experiencing some lesser degree of SAD or light hunger. Most persons affected note marked relief from their symptoms of depression after exposure to sunlight, for instance during and following winter vacations to sunny climates.

Current scientific research in the physiology behind this phenomenon points to the effect of light on the retinohypothalamic tract in either suppressing or stimulating of certain neurotransmitters, i.e. melatonin and serotonin respectively, known to be responsible for neuroendocrine changes of circadian rhythm in animal models and of mood and affect in human models. While current light therapy utilizing stationary indoor apparatus is being applied to patients with bipolar type II SAD in psychiatric clinical settings, it is felt by the inventor that the normal individual experiencing the common "winter blues" would receive benefit from a portable light source administering experimentally determined minimal doses of light to suppress melatonin, thus producing an anti-depressant effect.

Detailed information on the neurophysiology of daily exposure to light on both animal and human models is presented in *Science*, Lewy et al, 1980; 210:1267.

There are devices in the prior art providing light exposure for the treatment of SAD, but these devices are large, bulky, stationary metal enclosures having banks of fluorescent daylight tubes commonly referred to as "light boxes". The proposed invention is a full spectrum portable light source of 5000° K. sufficient power to deliver a premeasured dose of light of at least 500 lux over a period of time from a position indirect to the user's eyes. In effect with this invention, the user is exposed only to the type and amount of light he would experience if he were in a bright, sunny environment.

The present invention is an improvement over existing fixed devices in that it provides a portable light source worn on the user's head, not only for therapeutic outpatient use by those individuals suffering from SAD, but for a person living in those latitudes and geographic locations that experience prolonged, low-sunlight winter conditions. It is anticipated that some percentage of the population experiences SAD in such mild to moderate severity that their condition goes undiagnosed because it did not warrant psychiatric consultation. It is this group that will benefit from the proposed invention in the form of elevated mood, better overall performance, less susceptibility to stress and consequent depression, and higher energized levels for all activities of daily living. Insofar as this effect will be achieved by natural physiologic process using full spectrum light as neuroendoctrine stimulant, it is emphasized that the user would experience no ill effect than he normally would upon being exposed to natural sunlight of the same duration and intensity.

Accordingly, it is an object of the invention to provide an improved method of treating Seasonal Affective Disorder.

It is a further object to provide an improved method to treat Seasonal Affective Disorder that is effective, easy to use and will not interrupt the user from performing other normal daily functions.

Other objects and advantages of the invention will appear from the following detailed description of preferred embodiments of the invention, reference being made to the accompanying drawings.

SUMMARY OF THE INVENTION

In accordance with the present invention there is provided an improved method for therapeutic treatment of Seasonal Affective Disorder commonly called "winter blues" or "cabin fever" involving use of a head support means, a full spectrum light source means affixed to a visor included in the head support means, the light source being thereby positioned above the wearer's line of sight but so as to enable incident light to enter the eyes of the wearer. The light source generates sufficient light so that 1000 lux enters the wearer's eye in a manner similar to nature outdoor light emmitted by the sun.

DETAILED DESCRIPTION OF THE INVENTION

Figure 1:
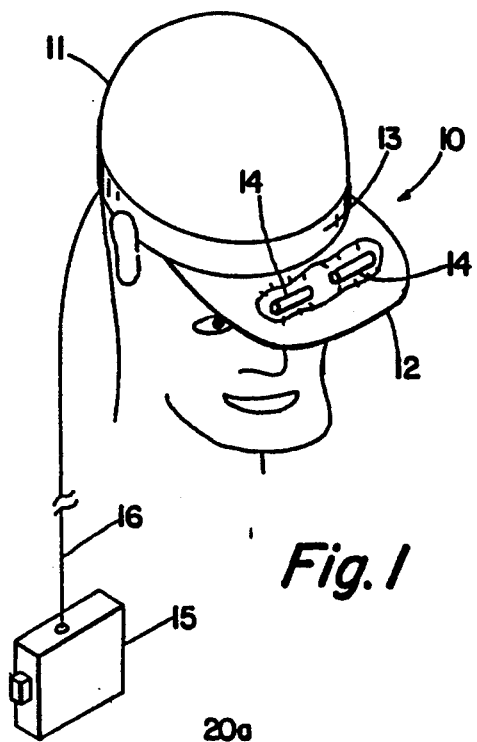
FIG. 1 is a perspective view of one embodiment of a cap mounted light source according to the present invention.

Referring to FIG. 1 there is illustrated one embodiment of the portable photoneuronic energizer used in the method of the invention, the portable energizer shown generally at 10. A fabric or polystyrene cap 11 having a visor 12 is shown being worn by a user person. The cap 11 has a flexible band 13 made of plastic material of sufficient strength to support the visor 12 which holds lamp 14. A typical material for the band 13 would be polystyrene.

One or more lamps 14 are affixed to the visor 12 as shown in FIG. 1 made of a material such as polystyrene that is rigid and of sufficient strength to support the lamp(s) as shown in FIG. 1 one may be sufficient, or more may be used depending on manufacturing specifications. The light source 12 must be capable of providing light intensity of at least 500 lux. Further, the light required must be full spectrum approximating natural outdoor daylight at a range of 5000° K. to 7000° K. color temperature. Full spectrum fluorescent bulbs or tubes as described in U.S. Pat. No. 3,670,193 are required wherein light is emitted in the wavelength of $400 \times 10^{-9}$ nanometers (red) to $740 \times 10^{-9}$ (violet) at said temperature range 5000° K. to 7500° K.

Fluorescent light bulbs that simulate the full color spectrum and generate the approximate ultraviolet microwatts, per lumen of natural sunlights are required by the present invention for the successful treatment of persons suffering from Seasonal Affective Disorder.

Figure 2:
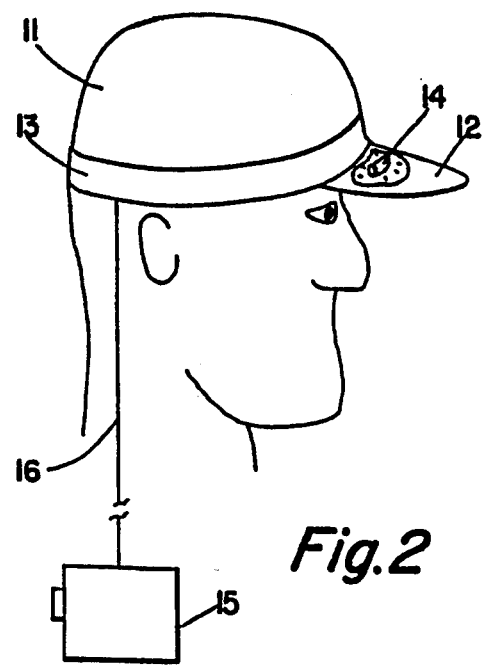
FIG. 2 is a side view of FIG. 1.

The position of said light source means is such that indirect light emitted will enter the eyes of the user suffering from Seasonal Affective Disorder. This is, light incident or indirect to the retina will enter in a manner similar to natural outdoor light emitted by the sun. It is the absence of this incident sunlight in Northern environments that leads to Seasonal Affective disorder or "cabin fever". The position of lamps 14 on visor 12 as shown in FIG. 1 and FIG. 2 produce said incident light similar to outdoor sunlight.

Power for illuminating lamps 12 is transmitted from D.C. electric battery source 15 by means of two insulated electrical wires 16. An electric batter of sufficient voltage Direct Current that would deliver ample power for providing 15-40 watts to illuminate the lamps 14 above to provide 535 to 2340 lux at 5000° K. to 7500° K. which approximate natural sunlight.

Figure 3:
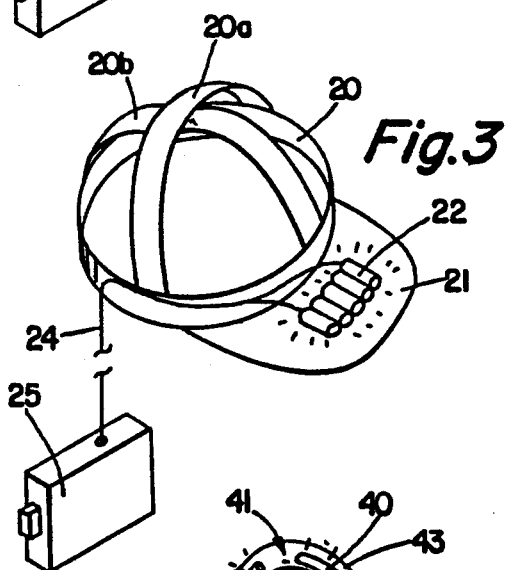
FIG. 3 is a perspective view of a second embodiments showing a head clamp with a visor of the invention.

In FIG. 3 there is shown a second embodiment of the invention having a head band clamp 20 with a visor 21 typically made of polystyrene as stated above. Also connected to head band clamp 20 are dome strips 21 and 22 to prevent slipping down over the user's head. Visor 21 has fluorescent bulbs (tubes) mounted at 22 to provide incident light as stated above Power from D.C. battery (12-30 volts) is transmitted to lamp 22 through electrical wires 24.

Figure 4:
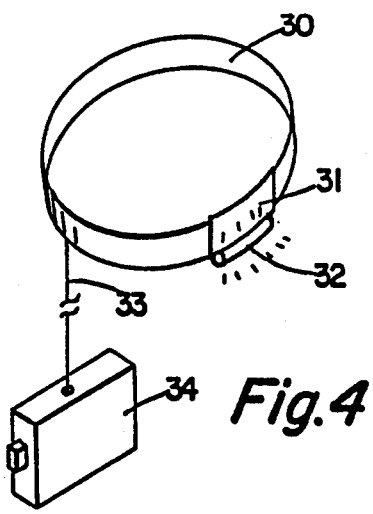
FIG. 4 is a perspective view of a third embodiment showing a head clamp mounted light source.

FIG. 4 shows a third embodiment of the invention showing a further head support means having a head band 30, a mounting plate 31 affixed to said head band 30, a full spectrum lamp 32, electrical wires 33 and electrical storage batter 34.

Figure 5:
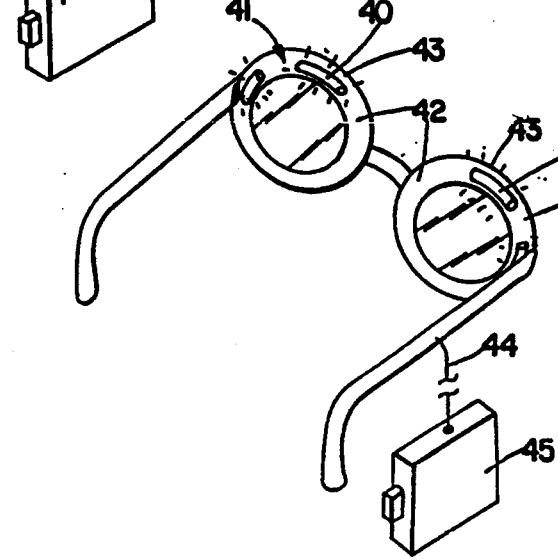
FIG. 5 is a perspective view of a fourth embodiment showing a light source mounted on eyeglass frames.

In FIG. 5 there is shown a fourth embodiment of the invention wherein said light source means are fluorescent bulbs (tubes) 40 affixed to eyeglass frame 41 on the eye rims 42 at the top 43. Again, the lamps 40 are illuminated by power from an electric storage batter 45 of 12 V to 40 V D.C. through electric conducting wires 44. The storage battery could be placed in a pocket of clothing worn by the user person or clipped to a belt.

While specific embodiments of the invention have been described and illustrated, it is to be understood that these embodiments are provided by way of example only and that the invention is not to be construed as being limited thereto, but only by the proper scope of the following claims:

I claim:

1. A method for treating a patient for light responsive psychological and/or psychiatric conditions comprising the steps of:
   mounting a head visor means on the head of the patient, said head visor means when mounted comprising a support having an upper and lower side, said support being fixed above and forward of the patient's eyes;
   mounting light projecting and light generating means to said support at said lower side thereof;
   generating a steady beam of light from said mounting light generator means sufficient to reach the patient's eye at an intensity of at least 1,000 lux and directing said steady beam of light into the eye of the patient by said mounted projecting means in a manner so as to avoid interfering with the patients field of vision.

* * * * *